Figure 1:
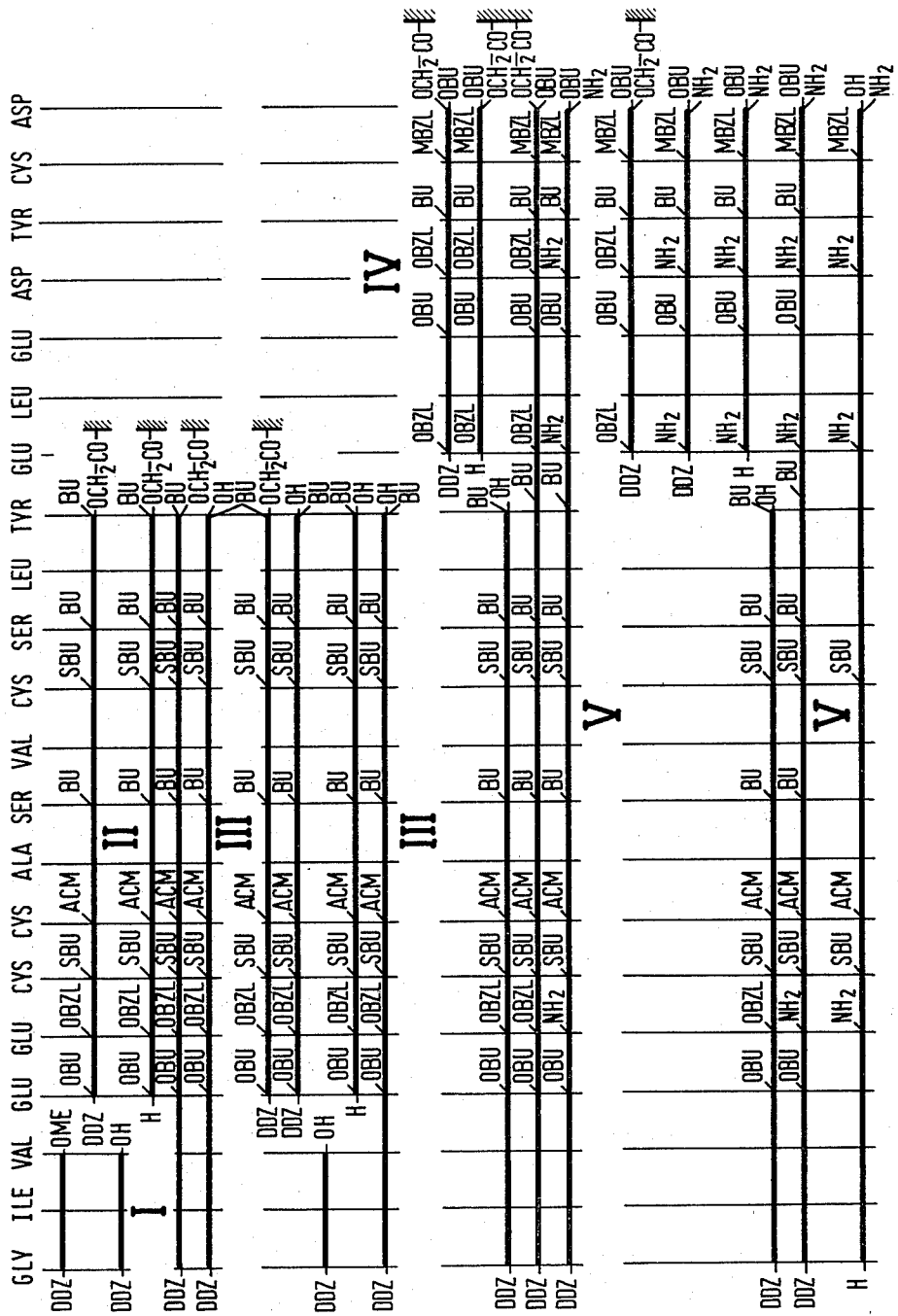

United States Patent [19]

Birr

[11] 4,351,764

[45] Sep. 28, 1982

[54] PROCESS FOR THE SELECTIVE FORMATION OF DISULFIDE BRIDGES IN POLYPEPTIDES AND THERAPEUTIC COMPOSITIONS

[75] Inventor: Christian Birr, Leimen/St. Ilgen, Fed. Rep. of Germany

[73] Assignee: der Wissenschaften e.V. Max-Planck-Gesellschaft zur/Forderung, Gottingen, Fed. Rep. of Germany

[21] Appl. No.: 158,021

[22] Filed: Jun. 9, 1980

[30] Foreign Application Priority Data

Jun. 12, 1979 [DE] Fed. Rep. of Germany ....... 2923787

[51] Int. Cl.³ ............................................ C07C 103/52
[52] U.S. Cl. ........................... 260/112.7; 260/112.5 K
[58] Field of Search ....................... 260/112.7, 112.5 R

[56] References Cited

U.S. PATENT DOCUMENTS

B471,617  2/1976  Kamber et al. ................. 260/112.7
3,883,500  5/1975  Geiger et al. ................... 260/112.7
4,029,642  6/1977  Obermeier ...................... 260/112.7

Primary Examiner—Delbert R. Phillips
Attorney, Agent, or Firm—Felfe & Lynch

[57] ABSTRACT

A process for the selective formation of at least two disulfide bridges in a polypeptide which process comprises treating a polypeptide starting material carrying at least two SH-groups to mask at least one of said SH-groups with a p-methoxybenzyl protective group and to mask at least one of the SH-groups with an acetamido methyl protective group, then splitting-off said p-methoxybenzyl protective group with pyridine-polyhydrogen fluoride in the presence of anisol, and then treating with iodine in an acid solution to produce said disulfide bridge-containing polypeptide.

24 Claims, 6 Drawing Figures

PROCESS FOR THE SELECTIVE FORMATION OF DISULFIDE BRIDGES IN POLYPEPTIDES AND THERAPEUTIC COMPOSITIONS

The invention relates to a process for the selective formation of two or more disulfide bridges in synthetic and/or natural polypeptides and more specifically in the production of insulin derivatives. In further aspect, the invention relates to therapeutic compositions which contain, as active ingredients, the insulin derivatives obtained in this manner.

Recently, the biological insulin synthesis by means of *Escherichia coli*-mutants has caused considerable sensation (see D. V. Goeddel, D. G. Kleid, F. Bolivar, H. L. Heynecher, D. G. Yansura, R. Crea, T. Hirose, A Krazewski, K. Itakura, and A. D. Riggs, *Proc. Natl. Acad. Sci. USA* (76) [in press]). Because of the danger of infection in men with insulin-producing bacteria, in the process, the insulin A- and B-chains are built up separately from each other in different cultures and are obtained as free polypeptide chains. They are then linked to the insulin molecule by a bridge by means of statistical disulfide-oxidation, as is also the case in the earlier total synthesis of insulin (R. E. Humbel, H. R. Bosshard, and H. Zahn in D. F. Steiner and N. Freinkel, *Handbook of Physiology*, Vol. 1 (Baltimore: Williams & Wilkins, 1972), pp. 11 ff.). In this statistical combination of the two chains, however, insulin is formed as only one product amony many possible ones (3 monomeric bi-disulfides of the A-chain, 1 disulfide of the B-chain, 12 isomeric insulins, and many oligomers and polymers of the individual and of both chains), so that thus far, it has not been possible to combine the A-chain and the B-chain into insulin by means of disulfide synthesis in yields higher than 10 to 20%. Even recombination attempts with natural A- and B-chains in the proportion of 1:1 produced insulin yields of only about 10%.

B. Kamber et al. have already reported on a total synthesis of human insulin in which the three disulfide bridges were, for the first time, aimed at different steps of a fragment-like synthesis (*Helvetica Chimica Acta*, Vol. 57 (1974), Fasc. 8, pp. 2617–2621 and Vol. 60 (1977), Fasc. 1, pp. 27–37, and the places in the literature cited there). Even in this case, two of three disulfide bridges of peptide chains A and B of the insulin were not formed first by linking these two complete chains, but in preliminary steps of the synthesis.

Along with the size and complexity of the peptide chains A and B that form the hormone insulin, the problem of insulin synthesis, therefore, is characterized, first of all, in that the three disulfide bridges linking the molecule intrachenarically and interchenarically should be formed by targeting, and not statistically, in order to increase the insulin yields. In so doing, one should be able to proceed, as much as possible, from biologically formed A-chains and B-chains of insulin.

Human insulin corresponds to the following formula I:

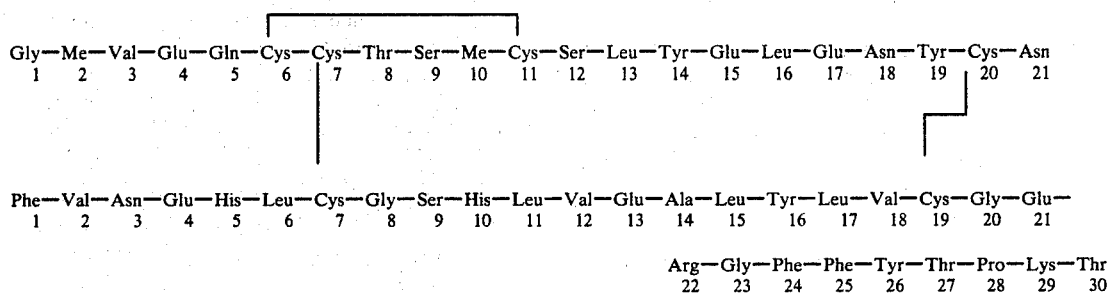
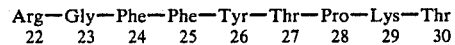

In Formula I above, the upper amino acid sequence (1 to 21) corresponds to the A-chain, while the lower amino acid sequence (1 to 30) represents the B-chain of human insulin.

The aim of the present invention consists in indicating a process that succeeds in selectively forming two or more disulfide bridges in natural and/or synthetic polypeptides, and does this, if necessary, in the presence of one or several already existing disulfide bridges, and at the same time, this process is said to be especially suited for the production of synthetic or semisynthetic human insulin by combining a synthetic A-chain of insulin with a synthetic or natural B-chain of insulin.

It was now found that one is successful in selectively forming disulfide bridges, if specific amino acid-protective groups are used, and these are split off again in a specific manner while simultaneously forming disulfide bridges. Thus, it has become evident in a surprising manner that if one or both SH-groups that are supposed to be converted into a first disulfide bridge are masked with a p-methoxybenzyl protective group, and one or both or additional SH-groups, which are supposed to be converted into a second or additional disulfide bridges, are masked with an acetamido methyl protective group, and the p-methoxybenzyl protective group is then split off with pyridine-polyhydrogen fluoride (HF/pyridine in the presence of anisol, and then treated with iodine in acid solution, by means of which the first disulfide bridge is formed, after which the acetamido methyl protective groups are split off, and the SH-groups set free in this manner are oxidized to the second or additional disulfide bridges.

The subject of the present invention, therefore, is a process for the selective formation of two or more disulfide bridges, if necessary in the presence of one or several already existing additional disulfide bridges, in synthetic and/or natural polypeptides, a process that is characterized in that at least one of the two SH-groups that are to be converted to a first disulfide bridge is masked with a p-methoxybenzyl protective group, and at least one of the two or of several SH-groups that are to be converted into a second or several disulfide groups is masked with an acetamido methyl protective group, and the p-methoxybenzyl protective group or groups are then split off with pyridine-polyhydrogen fluoride (HF/pyridine) in the presence of anisol, and then treated with iodine in acid solution.

In accordance with a preferred form of carrying out the present invention, the process is applied to the preparation of active human insulin, for which a synthetic insulin A-chain that exhibits an acetamido methyl protective group in the $A^7$-position and a p-methoxybenzyl protective group in the $A^{20}$-position is caused to react with an equimolar quantity of synthetic or natural, reduced insulin B-chain.

In so doing, it is advantageous to use an insulin B-chain that exhibits an acetamido methyl protective group in the $B^7$-position and a p-methoxybenzyl protective group in the $B^{19}$-position, since in this way, the formation of insulin isomers can be completely suppressed.

In this manner, it is possible to selectively link the four SH-groups that are to be combined with the correct reaction partner in each case, with the formation of two disulfide bridges, without, in so doing, endangering the already existing disulfide linkages, like the little intrachenaric disulfide ring $[A^6-A^{11}]$ that is already present in the A-chain.

In the process for the preparation of semisynthetic insulin according to the present invention that is preferred, one proceeds from a completely synthetic A-chain that exhibits four SH-groups, two of which are to be bound to the small intrachenaric disulfide ring, and are masked with tertiary-butyl mercapto protective groups, while the other two SH-groups exhibit a p-methoxybenzyl group or an acetamido methyl group, namely in the $A^{20}$- or $A^7$-positions. In so doing, the tertiary-butyl mercapto groups are first selectively split off by treatment with tributyl phosphane under nitrogen, after which the disulfide bridge, by means of selective oxidation with air, is closed intrachenarically, with the formation of the small ring. With this method of treatment, the acetamido methyl protective group and the p-methoxybenzyl protective group remain unaffected. Then, in accordance with the process that is according to the present invention, the p-methoxybenzyl protective group is split off by means of treatment with pyridine-polyhydrogen fluoride (HF/pyridine), and in so doing the acetamido methyl protective group is preserved. Then treatment is carried out with iodine in 30% acetic acid solution, in the presence of a natural B-chain of insulin in which the two SH-groups are unprotected. In so doing, the following steps are carried out in succession. First, the second disulfide bridge is linked ($A^{20}$-$B^{19}$), then the acetamido methyl protective group is split off, and the SH-group liberated in the process, along with the additional free SH-group of the B-chain that still remains, is oxidized to the third disulfide bridge ($A^7$-$B^7$). In so doing, it has turned out that, in a surprising way, about 30% of the quantity of of free B-chain employed reacts selectively with the correct SH-group of the B-chain.

In order to control the disulfide-bridging reaction even more exactly, however, it is undoubtedly possible to proceed from a natural or synthetic insulin B-chain which exhibits an acetamido methyl protective group in the $B^7$-position and a p-methoxybenzyl protective group in the $B^{19}$-position, so that the corresponding SH-groups of the A- or B-chain of the insulin are correspondingly masked, and then in carrying out the required procedure in the indicated reaction sequence, only one SH-group in each of the two chains is available for the reaction.

In accordance with this principle of the process according to the present invention, it is also possible, naturally, to form two different rings within a single chain via disulfide bridges, or to build two or several disulfide bridges in one or several chains. In this case, too, the SH-groups to be brought together for reaction with each other are protected with masking groups of the same kind, according to the present invention.

The process according to the present invention is of special significance in the synthesis of human insulin. In the various insulins, as a rule and according to their origin, the B-chain, aside from the C-terminus, is identical with the B-chain of human insulin, while the A-chains are clearly different. Since the C-terminus of the B-chain can easily be exchanged, it is sufficient to synthesize the A-chain and insert a B-chain of natural origin after changing the C-terminus, in order to then form human insulin, proceeding from these starting materials in accordance with the procedure according to the present invention.

Figure 6:
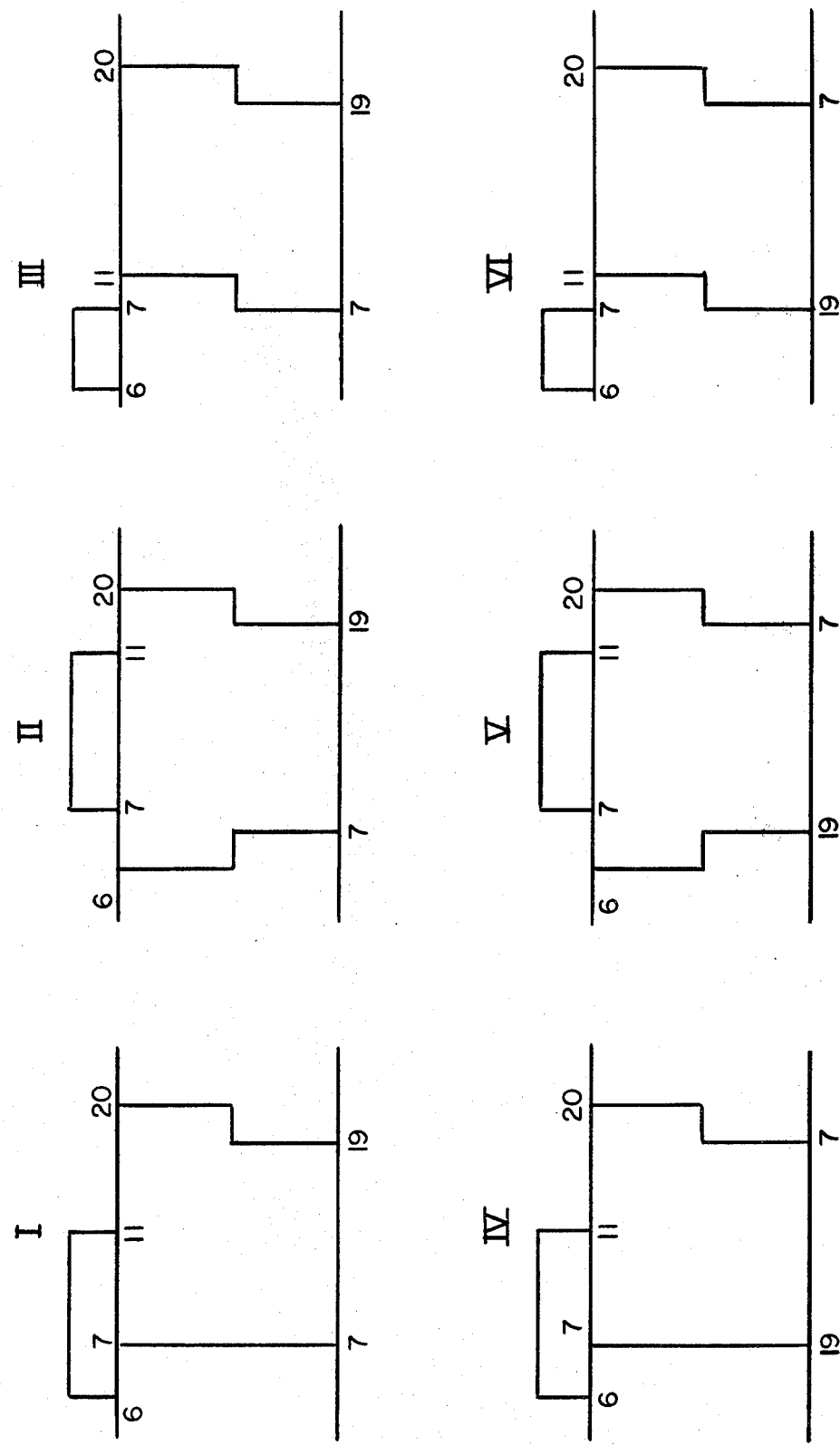

The procedure according to the present invention is, however, also suitable for the preparation of insulin analogs, as they are made clear, for example, in the schematic of FIG. 6.

As shown in FIG. 6, formula I to IV represent, in a schematized manner, the insulin derivatives which are accessible with the aid of the process according to the present invention. Thus, the general formula I stands for natural insulin, while formulas II and III represent insulin derivatives with an unnatural intrachenaric disulfide ring, in which the disulfide ring is present in the $A^7$-$A^{11}$-position or in the $A^6$-$A^7$-position. Formula IV to VI make clear the antiparallel variants of the compounds of the formulae I to III in which the insulin B-chain is bound antiparallel to the corresponding insulin A-chain.

These latter antiparallel variants of insulin with natural or unnatural arrangement of the intrachenaric disulfide bridge are of special significance, since, under certain pH conditions, they gradually reconstruct the natural form of bridging, so that they represent long-lived, inactive, synthetically produced storage forms of insulin which, under physiological conditions, are very slowly converted into active insulin, as is desirable in diabetes therapy.

For the production of the insulin analog of formula II ($[A^7-A^{11}, A^6-B^7$-cystine]-insulin), a synthetic $[A^7-A^{11}]$-insulin A-chain is used as the starting material, which has an acetamido methyl protective group in the $A^6$-position and a p-methoxybenzyl protective group in the $A^{20}$-position.

For the production of the insulin analog of formula III above ($[A^6-A^7, A^{11}-B^7, A^{20}-B^{19}$-cystine]-insulin), an $[A^6-A^7]$-insulin A-chain is used as the starting material, which exhibits an acetamido methyl protective group in the $A^{11}$-position and a p-methoxybenzyl protective group in the $A^{20}$-position.

For the production of the antiparallel insulin analog of formula IV above ($[A^6-A^{11}, A^7-B^{19}, A^{20}-B^7$-cystine]-insulin), a natural or synthetic $[A^6-A^{11}]$-insulin A-chain is used as the starting material, which exhibits an acetamido methyl protective group in the $A^7$- or $A^{20}$-position and a p-methoxybenzyl protective group in the $A^{20}$- or $A^7$-position, which is converted with a natural or synthetic insulin B-chain that is present in reduced form, or more preferably exhibits an acetamido methyl protective group in the $B^{19}$ - or $B^7$-position and a p-methoxybenzyl protective group in the $B^7$- or $B^{19}$-position.

For the production of the antiparallel insulin analog of formula V above ($[A^7-A^{11}, A^6-B^{19}, A^{20}-B^7$-cystine]-insulin), a synthetic $[A^7-A^{11}]$-insulin A-chain, which exhibits an acetamido methyl protective group in the $A^6$- or $A^{20}$-position and a p-methoxybenzyl protective group in the $A^{20}$- or $A^6$-position, is converted with a natural or a synthetic insulin B-chain that is present in reduced form, or more preferably, exhibits an acetamido methyl protective group in the $B^{19}$-position or $B^7$-position and a p-methoxybenzyl protective group in the $B^7$- or $B^{19}$-position.

For the production of the antiparallel insulin analog of formula VI above ([$A^6$-$A^7$, $A^{11}$-$B^{19}$, $A^{20}$-$B^7$-cystine]-insulin), a synthetic [$A^6$-$A^7$]-insulin A-chain, which exhibits an acetamido methyl protective group in the $A^{11}$- or $A^{20}$-position and a p-methoxybenzyl protective group in the $A^{20}$- or $A^{11}$-position, is converted with a natural or synthetic insulin B-chain that is present in reduced form, or more preferably, exhibits an acetamido methyl protective group in the $B^{19}$- or $B^7$-position and a p-methoxybenzyl protective group in the $B^7$- or $B^{19}$-position.

The object of the present invention is, furthermore, a process characterized in that a natural or synthetic insulin A-chain, with the intrachenaric disulfide ring in the $A^6$-$A^{11}$-position, the $A^7$-$A^{11}$-position, or in the $A^6$-$A^7$-position, in a parallel or antiparallel manner connected to a natural or synthetic insulin B-chain that is present in reduced form or exhibits acetamido methyl protective groups or p-methoxybenzyl protective groups in the positions defined above is linked by means of a reactive anchor bond to a polymeric carrier. In the process, an especially long-lived, unphysiological storage form of insulin is obtained that is of great advantage for purposes of therapeutic application.

In carrying out the process according to the present invention, the formation of the disulfide bridge is effected by means of oxidation with iodine, preferably in 30% aqueous acetic acid.

The splitting off of the p-methoxybenzyl protective group or groups is advantageously effected in such a way that the reagent pyridine/polyhydrogen fluoride (HF/pyridine) is used as the solvent.

The use of pyridine-polyhydrogen fluoride (HF/pyridine) as an agent for splitting off protective groups in peptide chemistry is already known (see *J. C. S. Chem. Comm.* (1976), pp. 451 and 452). It could, however, not be expected that the splitting off of the p-methoxybenzyl protective group in the presence of anisol as a cation-catcher succeeds especially smoothly, and this is without the influence of the acetamido methyl protective group which is still available, and without the influence of the disulfide bridges which may, perhaps, already be available.

In what follows below, the present invention is explained in detail with respect to the synthesis of bovine insulin. In so doing, first, the fragment synthesis, which is known in itself, of an insulin A-chain, with sulfur protective groups that can be selectively split off, to a polymeric carrier, as well as the conversion, according to the present invention, of this synthetic A-chain, under the gradual, oxidative, disulfide bridge formation with a natural B-chain, into a fully active, crystalline bovine insulin is explained. The concept applied in doing this is a further development of the principles that led to the synthesis of the MCD-peptide (C. Birr and W. Wengert-Müller, *Angewandte Chemie* 91 (1979), p. 156 and German Published Patent 28 30 442.

In so doing, the following are used as sulfur protective groups: the disulfide with tertiary butyl mercaptan (StBu or SBU) on cysteine in the $A^6$- and $A^{11}$-positions, the acetamido methyl protective group (Acm or ACM) in the $A^7$-position, and the p-methoxybenzyl protective group (Mbzl or MBZL) in the $A^{20}$-position.

In the following, the present invention is explained in detail, with reference to the attached drawings.

Figure 2:
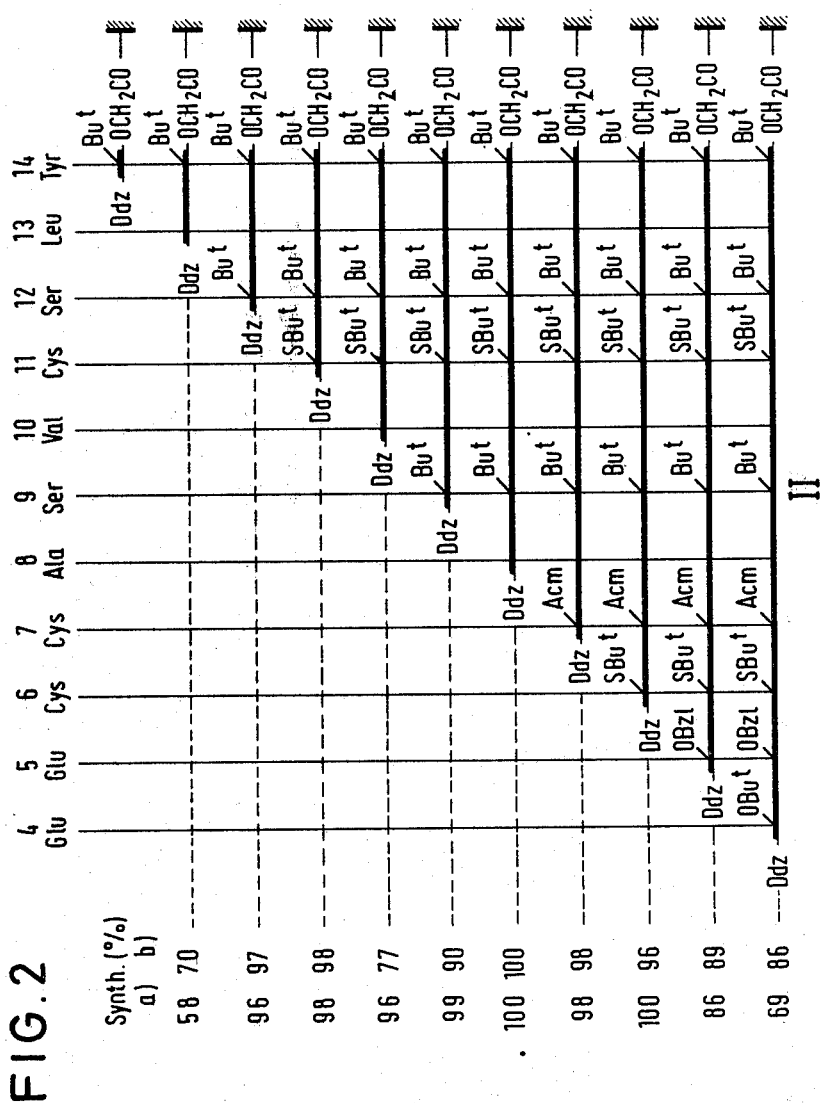
Figure 3:
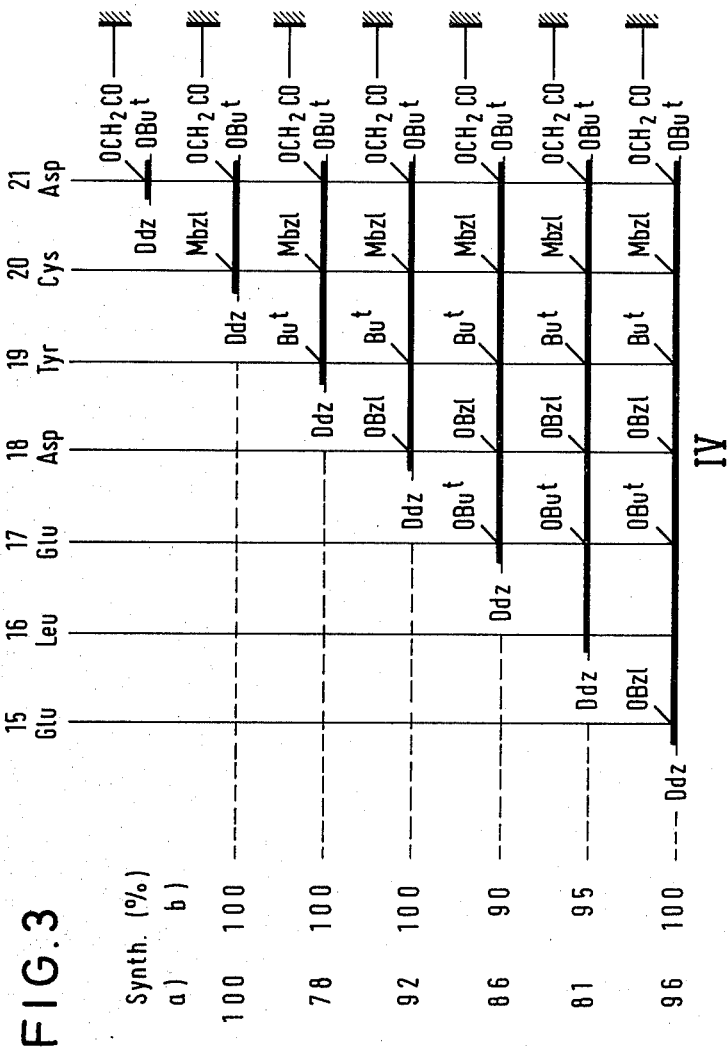
Figure 4:
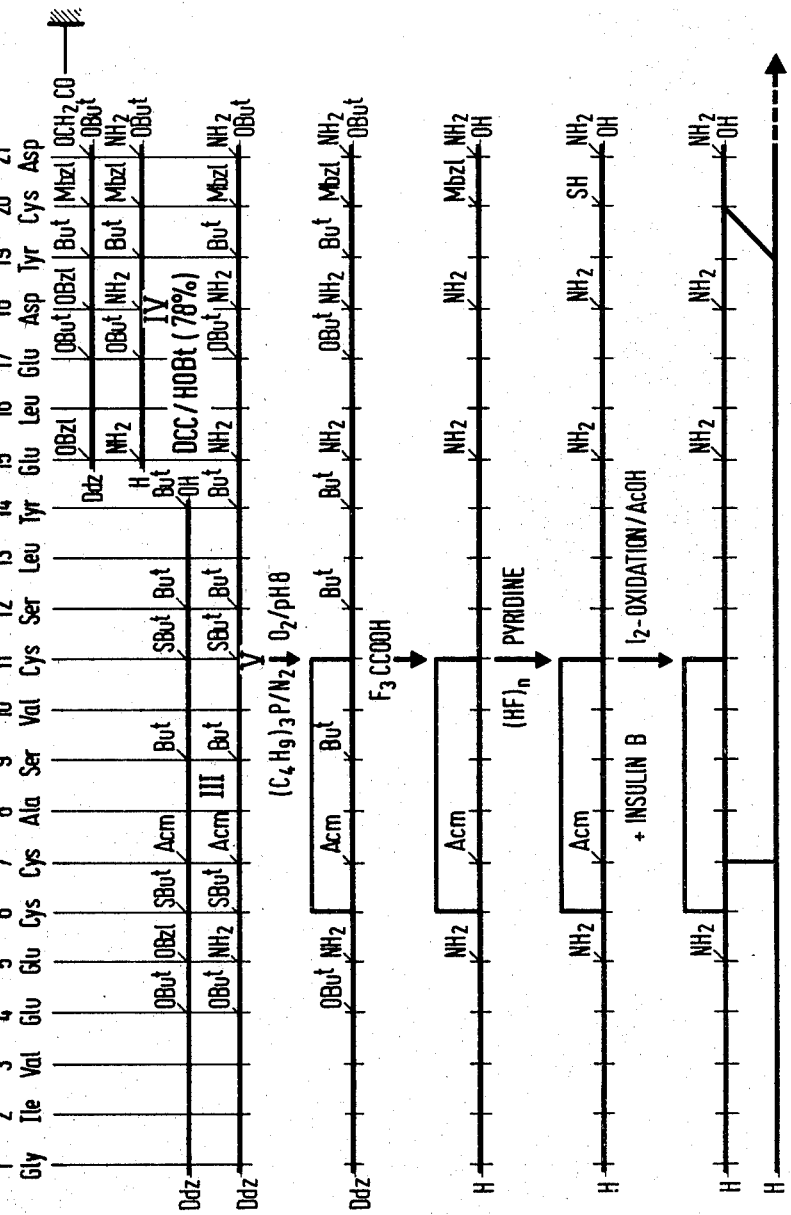
Figure 5:
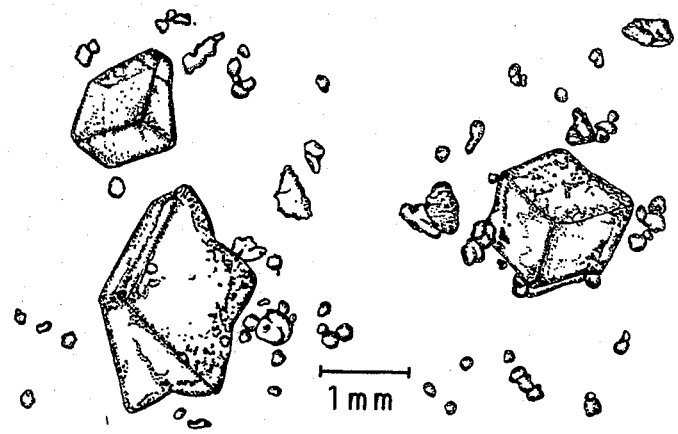

In the drawings:

FIG. 1 shows the total synthesis model of the insulin A-chain,

FIG. 2 the synthesis model of Fragment II of the insulin A-chain,

FIG. 3 the synthesis model of Fragment IV of the insulin A-chain,

FIG. 4 the linking of Fragments III and IV, with the formation of the small intrachenaric disulfide ring, to the insulin A-chain and its linking, according to the present invention, with a bovine insulin-B chain, FIG. 5 photomicrography of the zinc complex of the semi-synthetic fully active bovine insulin prepared according to the present invention, FIG. 6 is a schematic representation of the manner in which the inventive procedure is suitable for the preparation of various insulin analogs.

The abbreviations indicated in FIGS. 1 to 4 have the following meanings:

DDZ or Ddz = $\alpha,\alpha$-dimethyl-3,5-dimethoxy-benzyloxycarbonyl group,
OME = methoxy group,
OBU or OBu$^t$ = tertiary-butoxy group,
OBZL or OBzl = benzyloxy group,
SBU or SBu$^t$ = butyl mercapto group, tef.
ACM or Acm = acetamido methyl group,
BU or Bu$^t$ = butyl group, tef.
MBZL or Mbzl = p-methoxybenzyl group.

The preparation of the individual Fragments I, II, III, and IV was reported by C. Birr in Danzig in 1978.

Fragment I (1-3) is formed from Ddz-amino acids in solution, with a yield of 84%, according to a method that was recently published (C. Birr et al., *Int. J. Peptide Protein Res.* 13 (1979), pp. 287-295). Fragments II (4-14) and IV (15-21) [see the models represented in FIGS. 2 and 3] are built up on a polystyrene gel cross-linked with 0.5% divinyl benzene. Referred to the initial charge, yields of 90% (Fragment II) or 93% (Fragment IV) are obtained. All the synthesizing measures in the production of the fragment and their condensation on the polymeric carrier are continually controlled with a recording instrument, photometrically, by means of the spectroscopic properties of the acid-labile, temporarily N-terminal Ddz-protective group (C. Birr in Y. Wolman, *Peptides* 1974 New York; Halsted Press, 1975), pp. 117 ff.

Asp (OBzl) or Glu (OBzl) are inserted in the 5-, 15-, and 18-positions in place of Asn and Gln, in order to avoid a nitrile formation at the amide-side function by the dicyclohexylcarbodiimide-condensation reagent. In C-terminal Fragment IV, Asp (OH)OBu$^t$ with its $\beta$-carboxyl function is bound to the aromatic substances of the polystyrene carrier via an electrophile 2-oxoethyl-ester linkage. In this manner, all the future amide-side functions can be introduced simultaneously at the end of the synthesis by means of an ammonolysis of the designated benzyl- and 2-oxoethyl ester linkage in the separation of Fragments IV or V from the polymeric carrier (see FIG. 4).

All the other side functions of the insulin A-chain are safely protected during the synthesis of the fragments by tertiarybutyl protective groups. By means of the condensation of Fragment I in a fifteen-fold excess, with the aid of the condensation reagent's dicyclo hexyl carbodiimide in dimethyl formamide with the carrier-bound Fragment II, Fragment III (1-14) is formed on the carrier in a yield of 86% (referred to the II-gel polymer). By basic splitting of the 2-oxoethyl ester anchor bond of Fragment III on the polystyrol carrier (0.5 n-triethylamine in methanol/dioxane (1/1, volume/volume)+0.5% by volume 1 n aqueous sodium hydroxide solution)), followed by chromatographic purification of the separated, fully protected peptic acid, 1 g of the pure Fragment III is obtained (yield=59% [referred to the III gel polymer]). The stable existence of the benzyl ester in the $A^5$-position under the cleavage conditions was proved via the mass spectrum. C-terminal Fragment IV is split off from the carrier with dioxane saturated with ammonia, followed by a liquid ammonia/methanol mixture (4/1, volume/volume) under pressure at 20° C. After the chromatographic purification (DEAE A 25 Sephadex/methanol-0.5 n acetic acid (4/1, volume/volume) and Sephadex LG 20/methanol)), 1.45 g of the pure Fragment IV is obtained (yield=86%, referred to the carrier-linked preliminary stage). In model experiments, it has turned out that, under the conditions mentioned, at the C-terminal the $\beta$-amide of aspartic acid-$\alpha$-tertiary-butyl ester is formed, and not the succinimide derivative.

The condensation of 0.5 mMol of Fragment III with 1 mMol of Fragment IV to the fully protected Fragment V (1-21), with the aid of the carbodiimide-condensation reagent in dimethyl formamide (for a period of 4 days), results, after chromatographic purification, in 1.3 g of Fragment V (which corresponds to a yield of 78%, referred to Fragment III). A similar condensation of Fragment III in a 2.4-fold excess with Fragment IV on the carrier, with the use of carbonyl diimidazole, results in a yield of Fragment V of 12%. At the same time, 50% of the excess of Fragment III can be recovered.

In Fragment V, the benzyl ester in the $A^5$-position is converted into the amide with ammonia in methanol under pressure.

Then the tertiary-butyl disulfides in the $A^6$- and $A^{11}$-positions are split by reduction with tributyl phosphane, according to the model represented in FIG. 4, and the intrachenaric disulfide ring $A^6$-$A^{11}$ is formed selectively by oxidation in air with a yield of 84% (referred to the fully protected Fragment V). Then all the tertiary-butyl ester and ether protective groups are split off with trifluoroacetic acid. In this stage, the synthetic insulin A-chain still has the sulfur protective groups only in the $A^7$ (Acm)- and $A^{20}$ (Mbzl)-positions. The p-methoxybenzyl protective group (Mbzl) is selectively split off with hydrogen fluoride in pyridine in the presence of anisol (with a yield of about 80%).

The insulin A-chain with a single cysteinyl-mercapto function ($A^{20}$) that has been obtained in this way is immediately dissolved in 30% acetic acid, an equimolar quantity of reduced, natural B-chain from bovine insulin (2 free SH-funtions) in an acetic acid solution is mixed with it, and it is oxidized with 0.1 n iodine solution. Along with the interchenaric formation of the disulfide bridge exclusively between the $A^{20}$-$B^{19}$-positions that has been aimed at, as a secondary step in so doing, the last still remaining acetamido methyl protective group (Acm) in the $A^7$-position is removed by iodolysis, and the second interchenaric disulfide bridge ($A^7$-$B^7$) is then also formed by oxidation.

Then chromatography is immediately carried out in 10% acetic acid with Sephadex G 50. In the process, bovine insulin is obtained by electrophoresis and thin-layer chromatography which migrates in a manner identical with that of the authentic comparison material, with a yield of 25%. The freeze-dried raw material shows an activity of 52% in fat cells in the biological lipogenesis test, and an activity of 65% in the competitive receptor binding test.

The material can be crystallized as a zinc complex, and shows the characteristic crystalline form of insulin (FIG. 5). After repeated gel chromatography with Biogel P6 in 1% acetic acid and ion-exchange chromatographie with carboxy methyl cellulose, the semisynthetic bovine insulin formed according to the present invention shows full biological activity in both test systems mentioned above.

It is immediately evident that in using the selectively cleavable sulfur protective groups only on the insulin A-chain, the yield of the combination when using the chains in the proportion of 1:1, as compared with the previously known statistical disulfide bridge formation, can already be improved by more than 100%. This method can even be significantly improved, if the $B^7$-positions are also protected with an acetamido methyl protective group and the $B^{19}$-positions with a p-methoxybenzyl protective group, and can then be selectively set free in the process according to the present invention.

The following example will serve for further explanation of the invention.

EXAMPLE

The individual steps of the peptide synthesis are carried out in an automatic synthesizing machine made by the Schwarz Bio Research Company, with the aid of a centrifugal reactor. Conversion control is carried out by measuring the UV-absorption at 280 nm and 230 nm, and is registered with a two-channel recording instrument.

(a) Synthesis of the Fragment Insulin 1-3 (Fragment I) in Solution (a)1 Synthesis of ValOMe

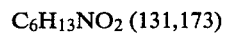

15.8 ml of thionyl chloride is added to 70 ml of methanol which is cooled in an ice/NaCl mixture to −5° to −10° C. Then 23.4 g of valine is added, during which the temperature should not rise above −5° C. The temperature is then slowly raised to 40° C., and stirring is carried out at this temperature for 2 hours. The mixture is then concentrated in a vacuum, and taken up in 5% $NaHCO_3$. It is then extracted with acetic ester, and the acetic ester phase is washed neutral with $H_2O$, and dried with $Na_2SO_4$. After evaporating in a vacuum at 40° C., the white residue is dried in a desiccator over $P_2O_5$.

Yield: 19 g: 80%.

Thin-layer chromatogram (n-butanol/glacial acetic acid/water; 4/1/1): Rf=0.46.

(a)2 Ddz-Ile-ValOMe (Mixed anhydride method)

$C_{24}H_{38}N_2O_7$ (466,577)

(1) Preparation of the amine component 2.6 g (20 mMol) of ValOMe is dissolved in 50 ml of $CH_2Cl_2$ and cooled to $-15°$ C.

(2) Preparation of the carboxyl component and coupling 7.3 g (20 mMol) of Ddz-Ile is dissolved in 50 ml of $CH_2Cl_2$ and treated with 2.21 ml (20 mMol) of N-methyl morpholine. The mixture is then cooled to $-15°$ C., activated by the addition of 2.24 ml (20 mMol) of chloroformic acid isopropyl ester (activation period 8 minutes), and the amine component is added all at one time.

(3) Work-up

The reaction mixture is extracted five times with ice-cold 0.1 n $KHSO_4$-solution, once with water saturated with NaCl, and five times with $KHCO_3$ solution. The solvent is dried with $Na_2SO_4$ and subjected to vacuum distillation. The remaining residue is dried over $P_2O_5$.

Yield: 7.4 g: 80%.

Thin-layer chromatogram (benzol/glacial acetic acid; 7/1: Rf=0.39

(a)3 Ddz-Gly-Ile-ValOMe $C_{26}H_{41}N_3O_8$ (523,630)

(1) Preparation of the amine component 7.4 g (16 mMol) of Ddz-Ile-ValOMe is dissolved in 100 ml of 5% trifluoroacetic acid in $CH_2Cl_2$. (The protective group is split off in 15 minutes.) The reaction solution is then neutralized with N-methyl morpholine (with pH-paper to pH 7-7.5), and cooled to $-15°$ C.

(2) Preparation of the carboxyl component and coupling 5.6 g (20 mMol) of Ddz-Gly is dissolved in 50 ml of $CH_2Cl_2$, and treated with 2.21 ml (20 mMol) of N-methyl morpholine. The reaction mixture is then cooled to $-15°$ C., activated by the addition of 2.24 ml (20 mMol) of chloroformic acid isopropyl ester (activation period 8 minutes), and the amine component is added all at one time.

(3) Work-up

The reaction mixture is extracted five times with ice-cold 0.1 n $KHSO_4$ solution, once with water saturated with NaCl, and five times with $KHCO_3$ solution. The solvent is dried with $Na_2SO_4$, and subjected to vacuum distillation. The remaining residue is dried over $P_2O_5$.

Yield: 7.1 g: 88%.

Melting point 147° C.

Amino acid analysis: HCl/propionic acid 15 minutes 160° C.

|  | Gly | Val | Ile |
|---|---|---|---|
| Calculated | 1 | 1 | 1 |
| Found | 1.10 | 1.00 | 1.01 |

Mass spectrum: m/e=523.

(a)4 Ddz-Gly-Ile-Val $C_{25}H_{39}N_3O_8$ (509,604)

7.1 g (14 mMol) of Ddz-Gly-Ile-ValOMe is dissolved in 20 ml of dioxane, and treated with 2 equiv. 1 n NaOH. The reaction mixture is stirred at room temperature, neutralized with 1 n acetic acid, concentrated in a vacuum, and purified by means of gel chromatography (Sephadex LG-20/methanol).

The saponification is carried on with thin-film chromatography: complete saponification.

Thin-layer chromatogram (chloroform/methanol/pyridine; 95/5/3): Rf=0.10.

O.R.D. value: $[\alpha]_D^{25} = +1.5$ (C=1.4) methanol.

(b) Automatic solid phase synthesis of insulin A-chain fragments 15-21 and 4-14 (IV or II)

| (1) 1 × | 2 min | Splitting off Ddz* with trifluoroacetic acid in $CH_2Cl_2$ |
|---|---|---|
| (2) 1 × | 15 min | |
| (3) 6 × | 2 min each | Washing with $CH_2Cl_2$ |
| (4) 1 × | 2 min | Repetition of the Ddz-cleavage with |
| (5) 1 × | 15 min | 5% trifluoroacetic acid |
| (6) 6 × | 2 min each | Washing with $CH_2Cl_2$ |
| (1-6) | | The filtrate of the cleavage product and the wash liquid are collected for photometric determination of the Ddz-cleavage product; conversion control |
| (7) 4 × | 2 min each | Reaction with triethyl amine [$CH_2Cl_2$/dimethylformamide (1/1)] 1:9 |
| (8) 12 × | 2 min each | Washing with $CH_2Cl_2$ |
| (9) 1 × | | addition of 20 ml of Ddz-amino acid solution (calculated on the basis of the preceding Ddz-values) in $CH_2Cl_2$ |
| (10) 1 × | | addition of 20 ml of dicyclo hexyl carbodiimide solution (same equivalents as Ddz-amino acid) in dimethyl formamide |
| (11) 1 × | | addition of 20 ml dimethyl formamide/$CH_2Cl_2$ (1/1) |
| (12) 1 × | 60 min | Reaction time |
| (13) 3 × | 2 min | Washing out with $CH_2Cl_2$ |
| (14) 5 × | 2 min | Washing out with $CH_2Cl_2$/methanol |
| (15) 4 × | 2 min | Washing out with $CH_2Cl_2$ |
| (16) Repetition of steps 9–15 twice | | |
| (17) 1 × | | addition of 40 ml 0.1 M 3-nitrophthalic acid anhydride in pyridine |
| (18) 1 × | | addition of 20 ml dimethyl formamide/$CH_2Cl_2$/(1/1) |
| (19) 1 × | 10 min | Reaction time |
| (20) 8 × | 2 min | Washing out $CH_2Cl_2$ |
| (21) 5 × | 2 min | Washing out with $CH_2Cl_2$/methanol (4/1) |
| (22) 4 × | 2 min | $CH_2Cl_2$ |
| (23) 5 × | 2 min | Washing out with $CH_2Cl_2$/methanol (4/1) |
| (24) 4 × | 2 min | Washing out with $CH_2Cl_2$ |

*Ddz = α,α-dimethyl-3,5-dimethoxy-benzyloxy-carbonyl group

The synthesizing program described above is used for the synthesis of insulin A 15-21 (Fragment IV) and A 4-14 (Fragment II). The carboxyl component (Ddz-amino acid) in each case is used in each cycle in fourfold excess, referred to the previous Ddz-value. Methylene chloride that has been purified over an $Al_2O_3$-column serves as a solvent and wash liquid for steps 1 to 9. The synthesis is started with 3 g of Ddz-AspOBu$^t$-polystyrene (cross-linked with 0.5% divinyl benzene) and 3 g of Ddz-Tyr(Bu$^t$) -polystyrene (cross-linked with 0.5% divinyl benzene) in a centrifugal reactor.

Charges:

0.526 mMol Ddz-AspOBu$^t$/g polymer
0.664 mMol Ddz-AspOBu$^t$/g polymer
0.900 mMol Ddz-Tyr(Bu$^t$)/g polymer
0.857 mMol Ddz-Tyr(Bu$^t$)/g polymer If no volume is indicated in the program, a volume of 60 ml is measured out at this point by the automatic synthesizing machine.

The conversions, referred to the initial charge, are found on the basis of photometric measurement of the Ddz-cleavage product as follows:

Conversion results insulin 15–21.

| | First Synthesis Charge mMol/g carrier | Conversion % | Second Synthesis Charge mMol/g carrier | Conversion % |
|---|---|---|---|---|
| AspOBu$^t$ | 0.526 | — | 0.664 | — |
| Cys(Mbzl) | 0.529 | 100 | 0.714 | 100 |
| Tyr(Bu$^t$) | 0.412 | 78 | 0.660 | 100 |
| Asp(OBzl) | 0.358 | 92 | 0.670 | 100 |
| Glu(OBu$^t$) | 0.308 | 86 | 0.593 | 90 |
| Leu | 0.250 | 81 | 0.563 | 95 |
| Glu(OBzl) | 0.240 | 96 | 0.600 | 100 |

See FIG. 2. The average yield of both syntheses amounts to 93%.

Conversion rresults insulin 4–14.

| | First Synthesis Charge mMol/g carrier | Conversion % | Second Synthesis Charge mMol/g carrier | Conversion % |
|---|---|---|---|---|
| Tyr(Bu$^t$) | 0.900 | — | 0.857 | — |
| Leu | 0.523 | 58 | 0.600 | 70 |
| Ser(Bu$^t$) | 0.502 | 96 | 0.591 | 97 |
| Cys(SBu$^t$) | 0.491 | 98 | 0.571 | 98 |
| Val | 0.470 | 96 | 0.442 | 77 |
| Ser(Bu$^t$) | 0.463 | 99 | 0.400 | 90 |
| Ala | 0.470 | 100 | 0.414 | 100 |
| Cys(Acm) | 0.466 | 99 | 0.407 | 98 |
| Cys(SBu$^t$) | 0.500 | 100 | 0.392 | 96 |
| Glu(OBzl) | 0.433 | 86 | 0.352 | 89 |
| Glu(OBu$^t$) | 0.300 | 69 | 0.300 | 86 |

See FIG. 3. The average yield of both syntheses is 90%.

The second synthesis is not interrupted after the tenth cycle, instead the conversion with insulin A 1–3 follows. In each case, the tripeptide is used in fivefold excess in 3 conversions. For this reaction, the synthesis program is changed as follows:

(9) 1×addition of 20 ml of Ddz-tripeptide solution (CH$_2$Cl$_2$)
(10) 1×addition of 20 ml 1-hydroxybenzotriazole solution (in dimethyl formamide)
(11) 1×addition of 10 ml of dicyclohexylcarbodiimide solution in dimethyl formamide/CH$_2$Cl$_2$ (1/1)
(12) 1×addition of 20 ml of CH$_2$Cl$_2$ dimethyl formamide (1/1)
(13) 1×4 hours reaction time
(14) 3×2 min washing out with CH$_2$Cl$_2$
(15) 5×2 min washing out with CH$_2$Cl$_2$/methanol (4/1)
(16) 4×2 min washing out with CH$_2$Cl$_2$
(17) Repetition of steps 9–16 twice.

In the condensation of the fragment, 15.75 mMol tripeptide 1 equivalent dicyclo hexyl carbodiimide, and 1.5 equivalents of 1-hydroxybenzotriazole are used in each cycle.

Conversion result insulin 1–14 (Fragment III).

| | Charge mMol/g carrier | Conversion % |
|---|---|---|
| Insulin A 4–14 | 0.300 | — |
| Insulin A 1–14 | 0.258 | 86 |

(c) Synthesis of the insulin A-chain to the polymeric carrier (c)1 Automated cleavage of the insulin Fragments II (4–14), III (1–14), and IV (15–21) from the polymeric carrier The cleavage takes place with modified Beyerman reagent (1 n triethylamine/methanol+1% 1 n aqueous NaOH)/dioxane (1:1), with the following synthesis program:

(1) 1×2 min peptide cleavage
(2) 3×4 min peptide cleavage
(3) 20×30 min peptide cleavage The whole cleavage reaction is continuously recorded by means of the photometric control device. The end of the cleavage reaction can be read from the recording. Most of the time, the cleavage is finished after about 3–6 hours. The filtrate is collected in a flask in which dry ice has been placed to neutralize the basic peptide solution. Since 3-nitrophthalic acid anhydride has been used in the synthesis as a blocker, the core sequences can be separated by means of a first fractionation with DEAE-ion exchanger A-25, using a mixture of methanol/0.5 n acetic acid (4/1). After this, a purification is carried out with column chromatography, using Sephadex LH-20 (2.5×200) and methanol as a vehicle.

(c)2
Ddz-Glu(OBu$^t$)-Glu(OBzl)-Cys(SBu$^t$)-Cys(Acm)-Ala-Ser(Bu$^t$)-Val-Cys(SBu$^t$)-Ser(Bu$^t$)-Leu-Tyr(Bu$^t$) [1]

C$_{94}$H$_{148}$N$_{11}$O$_{24}$ (1816,285)

After the separation and purification described above, the mixture of methyl ester and free acid of Fragment II (4–14) is subjected to saponification.

About 1.1 g of Fragment II (4–14) is dissolved in 3 ml of dioxane, and treated with 2 equivalents of 1 n NaOH. The pH of the solution is kept at 11.5 with a pH-stat. After 4 hours at room temperature, the reaction is concluded. Neutralization is then carried out with 1 n acetic acid, and concentration takes place in a vacuum. The removal of salt then follows by means of gel chromatography with Sephadex LH-20/methanol. Finally, drying is carried out over P$_2$O$_5$. The yield is 73% (1.1 g), referred to the last Ddz-value of the N-terminal amino acid of the heptapeptide bound to the carrier.

Thin layer chromatogram (n-butanol/glacial acetic acid/water; 4/1/1): Rf=0.83.

Mass spectroscopic evidence of the protective groups:

| Cleavage product of | Ddz | Acm | OBzl |
|---|---|---|---|
| m/e | 178 | 72 | 107 |

Amino acid analysis: (HCl/propionic acid, 15 minutes, 160° C.).

|  | Cys CysSO₃H | Ser | Glu | Ala | Val | Leu | Tyr |
|---|---|---|---|---|---|---|---|
| Calculated | 3 | 2 | 2 | 1 | 1 | 1 | 1 |
| Found | 2.38 | 1.82 | 1.64 | 1.10 | 1.13 | 1.00[a] | 0.95 |

[a]Reference amino acid

O.R.D. value: $[\alpha]_D^{25} = -38.2$ (C=0.5)MeOH.

(c)3
Ddz-Gly-Ile-Val-Glu(OBu^t)-Glu(OBzl)-Cys(SBu^t)-Cys(Acm)-Ala-Ser(Bu^t)-Val-Cys(SBu^t)-Ser(Bu^t)-Leu-Tyr(Bu^t). [2]

$C_{107}H_{171}N_{14}O_{27}$ (2085,634)

After the separation described, in general, above, and the purification operations, a separation of Fragment III (1–14) [2] takes place with sephadex LH-60/methanol. The mixture of methyl ester and free acid that is also not separated by this process is saponified in a manner analogous to that for Fragment II [1] again.

The yield is 59% (1.1 g), referred to the last Ddz-value of the N-terminal amino acid of the heptapeptide bound to the carrier.

Thin-film chromatogram (chloroform/methanol/glacial acetic acid; 85/15/5): Rf=0.63 (uniformly).

Mass spectroscopic evidence of the protective groups:

| Cleavage product of | Ddz | Acm | OBzl | Bu^t |
|---|---|---|---|---|
| m/e | 178 | 72 | 107 | 57 |

Amino acid analysis: 6 n HCl, 28 hours, 110° C.

|  | Cys CysSO₃H | Ser | Glu | Gly | Ala | Val | Ile | Leu | Tyr |
|---|---|---|---|---|---|---|---|---|---|
| Calculated | 3 | 2 | 2 | 1 | 1 | 2 | 1 | 1 | 1 |
| Found | 2.86 | 2.08 | 1.78 | 1.05 | 1.18 | 2.04 | 1.03 | 1.00[a] | 0.86 |

[a]Reference amino acid

Rotation value: $[\alpha]_D^{25} = -32.3$ (C=0.6 methanol).

This fragment is later put into solution for the condensation.

(c)4
Ddz-Glu(OBzl)-Leu-Glu(OBu^t)-Asp(OBzl)-Tyr(Bu^t)-Cys(MBzl)-AspOBu^t. [3]

$C_{81}H_{109}B_7O_{22}$ (1532,803)

After the separation and purification of Fragment IV (15–21) [3], the saponification is carried out in a manner analogous to that for Fragment II [1].

The yield is 51% (0.5 g), referred to the last Ddz-value of the N-terminal amino acid of the heptapeptide bound to the carrier.

Thin-film chromatogram (n-butanol/glacial acetic acid/water; 4/1/1): Rf=0.80.

Mass spectrometric evidence of the protective groups:

| Cleavage product of | Ddz | OBzl | MBzl | Bu^t |
|---|---|---|---|---|
| m/e | 178 | 107 | 121 | 57 |

Amino acid analysis: HCl/propionic acid, 15 minutes, 160° C.

|  | Asp | Glu | Leu | Tyr | Cys |
|---|---|---|---|---|---|
| Calculated | 2 | 2 | 1 | 1 | 1 |
| Found | 1.67 | 1.70 | 1.00[a] | 0.87 | 0.83 |

[a]Reference amino acid

Rotation value: $[\alpha]_D^{25} = -41.2°$ (C=2) methanol.

(c)5 Recoupling Fragment IV (Insulin 15–21) to the polymeric carrier

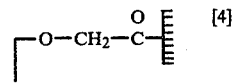

Ddz—Glu(OBzl)—Leu—Glu(OBu^t)—Asp(OBzl)—Tyr(Bu^t)—Cys(MBzl)—AspOBu^t. [4]

400 mg (0.26 mMol) insulin A 15–21 [3] is dissolved in 5 ml of methanol. Then 38.4 mg (0.23 mMol) of CsOH solution is added (10% shortage). The solvent is distilled off in a vacuum, and the residue is dried over $P_2O_5$.

For resin esterification, the dried cesium salt is dissolved in absolute dimethyl formamide, and added in fivefold excess to the resin (1.89 mMol Br/g resin) (634 mg). The charge is agitated for 3 days at 40° C. The resin is filtered off through a glass frit, and thoroughly washed with the following solvents: dimethyl formamide, chloroform, dioxane/methanol (3/1), methanol, dioxane and methanol. After that, it is dried in a desiccator over $P_2O_5$. The charge of the resin is determined by means of elementary analysis for nitrogen, by photometric analysis of the cleavage of the Ddz-protective group, and by quantitative amino-acid analysis. A quantitative amino-acid analysis showed a charge of 0.11 mMol/g of resin.

(c)6 Recovery of Fragment IV (15–21)

The various wash solutions are combined, and concentrated by evaporation on a rotary evaporator. The residue is dissolved in acetic ester, and converted into the free acid by extraction with 0.5 n $KHSO_4$ solution. The organic phase is then washed neutral with $H_2O$ and dried over $Na_2SO_4$. Further concentration then takes place by means of evaporation under vacuum on a rotary evaporator, and drying is carried out over $P_2O_5$. 200 mg of Fraction IV (insulin 15–21), which has been purified by means of thin layer chromatography, is recovered.

(c)7 Fragment condensation to Fragment III (insulin 1-14) in solution

Ddz-Gly-Ile-Val-Glu(OBu$^t$)-Glu(OBzl)-Cys(SBu$^t$)-Cys(Acm)-Ala-Ser(Bu$^t$)-Val-Cys(SBu$^t$)-Ser(Bu$^t$)-Leu-Tyr(Bu$^t$) [5]

$C_{107}H_{171}N_{14}O_{27}$ (2085,634)

763 mg (1.5 mMol) of Fraction I (insulin A 1-3), 270 mg (2 mMol) of 1-hydroxybenzotriazole and 0.22 ml (2 mMol) of N-methyl morpholine are dissolved in 20 ml of absolute dimethyl formamide. The solution is cooled to 0° C., and treated with 206 mg (1.0 mMol) of dicyclohexyl carbodiimide. The mixture is agitated for 1 hour at 0° C., and then 600 mg (0.35 mMol) of Fragment II (insulin A 4-14 [1])(adjusted to pH 7.5 with N-methyl morpholine) is added. Agitation is then carried out for 12 hours overnight, concentration then follows in a vacuum, and purification takes place by means of gel chromatography (Sephadex LH-20/methanol).

The yield amounts to 413 mg of Fragment III (insulin A 1-14), which corresponds to a conversion of 52%. Amino acid analysis: HCl/propionic acid, 20 minutes, 160° C.

|  | Cys CysSO$_3$H | Ser | Glu | Gly | Ala | Val | Ile | Leu | Tyr |
|---|---|---|---|---|---|---|---|---|---|
| Calcul. | 3 | 2 | 2 | 1 | 1 | 2 | 1 | 1 | 1 |
| Found | 1.66 | 1.64 | 1.99 | 1.02 | 1.00$^a$ | 2.21 | 0.93 | 1.04 | 0.65 |

$^a$Reference amino acid

O.R.D. value: $[\alpha]_D^{25} = -32.1$ C=0.1 methanol.

(c)8 Fragment condensation to Fragment V (insulin 1-21) on the polymeric carrier Ddz—Gly—Ile—Val—Glu(OBu$^t$)—Glu(OBzl)—Cys(SBu$^t$)—Cys(Acm)—Ala— [6]

—Ser(Bu$^t$)—Val—Cys(SBu$^t$)—Ser(Bu$^t$)—Leu—Tyr(Bu$^t$)—Glu(OBzl)—Leu—

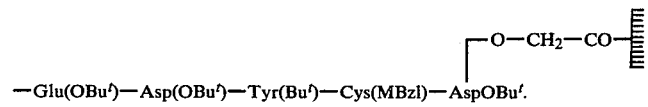

—Glu(OBu$^t$)—Asp(OBu$^t$)—Tyr(Bu$^t$)—Cys(MBzl)—AspOBu$^t$.

700 mg of insulin 15-21-phenacetyl resin [4] (charge 0.074 mMol) is placed in a shaking frit, and treated with 5 percent trifluoroacetic acid in $CH_2Cl_2$. Agitation takes place for half an hour, and then thoroughly washing out with $CH_2Cl_2$. This procedure is repeated twice. The shaking frit is then dried over $P_2O_5$. The peptide is deprotonized in the shaking frit with triethyl amine [$CH_2Cl_2$/dimethyl formamide (1:2)](1:3), and thoroughly washed with dimethyl formamide/$CH_2Cl_2$ and dimethyl formamide.

400 mg (0.18 mMol) of Fragment III (insulin 1-14 [5]) and 28 mg (0.17 mMol) of carbonyl diimidazole are dissolved in 5 ml of absolute dimethyl formamide at 0° C., and the solution is added to the above Fragment IV (15-21) which is bound to the carrier. Agitation is carried out for 4 days, the reaction solution is filtered off, and the resin is dried over $P_2O_5$. Fragment III (insulin 1-14) can be recovered, as described further below. A quantitative amino acid analysis, referred to alanin in Fragment III (insulin 1-14), shows a charge of 0.0086 mMol, that is 30 mg of insulin 1-21. This corresponds to a conversion of 11.6%. The conversion is repeated, but an increase in the conversion can not be attained.

Recovery of Fragment III (insulin 1-14)

The various wash solutions are combined, and evaporated under vacuum in a rotary evaporator. By adding water, excess imidazolide is converted into the free acid. Evaporation is carried out again (in the rotary evaporator), and drying follows. The residue is purified by gel chromatography with LH-20. 210 mg of Fragment III (insulin 1-14) is recovered.

(c)9 Separating the insulin A-chain from the polymeric carrier

Ddz-Gly-Ile-Val-Glu(OBu$^t$)-Gln-Cys(SBu$^t$)-Cys-(Acm)-Ala-Ser(Bu$^t$)-Val-Cys(SBu$^t$)-Ser(Bu$^t$)-Leu-Tyr(-Bu$^t$)-Gln-Leu-Glu(OBu$^t$)-Asn-Tyr(Bu$^t$)-Cys(MBzl)-AsnOBu$^t$. [1]

The polymeric carrier [6] is put into suspension with 10 ml of methanol in a steel cylinder. With the exclusion of humidity, the steel cylinder is cooled, and treated with 80 ml of liquid ammonia. In this way, the β-carboxyl function should be split off from its linkage to the phenacetyl carrier, and the β-benzyl ester groupings of the aspartic acid in position 18 should also be split, and the γ-benzyl ester grouping of glutamic acid in positions 5 and 15, and they should be converted in one step to the corresponding amide. The cylinder is sealed, and it is agitated for 3 days at room temperature.

After the cleavage reaction, the resin is filtered off, and thoroughly washed with methanol. An amino acid analysis of a resin sample in 6 n HCl at 160° C. for 20 minutes shows that the cleavage has proceeded completely. The cleavage solution is evaporated under a vacuum at 40° C., and re-dissolved in methanol. According to the thin-layer chromatographic control, the cleavage solution contains, along with the insulin A-chain that was aimed for, the fraction of Fragment IV (15-21 21) that was not converted. Besides, it remains an insoluble residue, which can not be dissolved even in acetic ester. An amino acid analysis is carried out on this solid residue. The analysis shows that the insoluble constituent consists of insulin A-chain. Since a mercaptan odor can be established, however, it can be assumed that the S-tertiary-butyl protective groups have been split off, in part, by the basic conditions, and the solid residue consists of oligomeric insulin A-chain (20 mg). The solid residue and the methanol solution are combined, and used for further reaction. The mixture is dried over $P_2O_5$.

Crude yield (methanol phase) about 80 mg.
Insoluble residue about 20 mg.

Thin-film chromatogram (n-butanol/glacial acetic acid/water; 4/1/1): Rf=0.9 (fragment 15-21), 0.2 (insulin A-chain)

(c)10 Formation of the intrachenaric disulfide bridge $A^6$–$A^{11}$

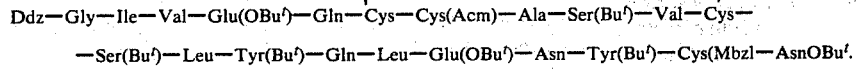

Ddz—Gly—Ile—Val—Glu(OBu$^t$)—Gln—Cys—Cys(Acm)—Ala—Ser(Bu$^t$)—Val—Cys— [8]

—Ser(Bu$^t$)—Leu—Tyr(Bu$^t$)—Gln—Leu—Glu(OBu$^t$)—Asn—Tyr(Bu$^t$)—Cys(Mbzl)—AsnOBu$^t$.

The peptide mixture [1] from the last cleavage (c)9) is used for the reduction of Cys 6 and Cys 20. The reduction is carried out with tributyl phosphane. Then the closing of the disulfide linkages takes place by oxidation in air.

30 mg of Fraction V (insulin 1–21) about 100 mg of mixture [1] are dissolved in 2.0 ml of propanol/water, and nitrogen is allowed to flow through. Then 4 μl of tributylphosphane is added. The reaction solution is allowed to react for 48 hours under nitrogen at room temperature.

Then all the reaction solution is poured into 1 l of water that has been adjusted to pH 8 with ammonia. Air is passed through the solution for 48 hours. It is then concentrated under a vacuum, and separation takes place by means of gel chromatography with LH-20. 20 mg of pure, fully protected insulin A-chain is obtained [8].

The yield of the closing of the inner ring amounts to 66%.

Amino acid analysis: HCl/propionic acid, 35 minutes, 160° C.

analysis in 6 n HCl at 160 C/20 minutes shows that the cleavage has completely run its course. The various cleavage reactions are worked up as follows.

A fractionation is then carried out with a mixture of methanol/0.5 n acetic acid (4/1), using a DEAE-A 25 ion exchanger. Purification follows, using column chromatography with Sephadex LH-20-column (2.5×200) cm, with methanol as a vehicle. The product of the cleavage with liquid ammonia contains two spots that run differently in the electrophoresis and on the DC-plate. It can be shown by dansylation that the Ddz protective group has been split off from a part of the peptide.

The yield in the cleavage with dioxan/ammonia is 700 mg (42%), referred to the last Ddz-value of the N-terminal amino acid of the heptapeptide bound to the carrier.

Thin layer chromatogram (chloroform/methanol/-glacial acetic acid; 85/15/5): Rf=0.7.

Thin-layer chromatogram (n-butanol/glacial acetic acid/water; 4/1/1): Rf=0.9.

The yield in the cleavage with liquid ammonia under pressure amounts to 0.75 g (44%), referred to the last Ddz-value of the N-terminal amino acid of the heptapeptide bound to the carrier.

Thin-layer chromatogram (chloroform/methanol, glacial acetic acid; 85/15/5): Rf=0.7 and 0.5.

Thin-layer chromatogram (n-butanol/glacial acetic

|  | Cys CysSO$_3$H | Asp | Ser | Glu | Ala | Val | Ile | Leu | Tyr | Gly |
|---|---|---|---|---|---|---|---|---|---|---|
| Calc. | 4 | 2 | 2 | 4 | 1 | 2 | 1 | 2 | 2 | 1 |
| Found | 3.05 | 1.86 | 2.12 | 4.10 | 1.03 | 2.00$^a$ | 0.87 | 2.24 | 1.87 | 0.97 |

$^a$Reference amino acid

O.R.D. value: $[\alpha]_D^{25} = -42°$ (C=0.1) methanol (d) The synthesis of insulin A-chain in solution (d)1 The separation of Fragment IV (insulin A 15–21) from the polymeric carrier Ddz-Gln-Leu-Glu(OBu$^t$)-Asn-Tyr(Bu$^t$)-Cys(MBzl)-AsnOBu$^t$. [9]

$C_{67}H_{100}N_{10}O_{19}$ (1349,560)

The cleavage, in which both the β-carboxyl function is converted from its linkage to the phenacetyl carrier to the amide and the ω-benzyl ester groupings of aspartic acid in position 18 as well as of the glutamic acid residue in position 15 to the amide, takes place with dioxane/NH$_3$. The whole cleavage is continuously controlled with an UV-photometer, and registered by a recording instrument. The end is indicated after two days. A quantitative amino acid analysis shows that only 50% of the peptide has been split off from the carrier.

The polymeric carrier is then put into suspension with 10 ml of methanol in a steel cylinder. With the exclusion of humidity, the cylinder is cooled to −70° C., and treated with 80 ml of liquid ammonia. The cylinder is sealed, and agitated for 3 days at room temperature. After the cleavage reaction, the resin is filtered off and thoroughly washed with methanol. An amino acid acid/water; 4/1/1: Rf=0.9 and 0.8

The total yield amounts to 86%) (1.45 g), referred to the last Ddz-value of N-terminal amino acid of the heptapeptide bound to the carrier.

Amino acid analysis: HCl/propionic acid, 15 minutes, 160° C.

|  | Asp | Glu | Leu | Tyr | Cys |
|---|---|---|---|---|---|
| Calc. | 2 | 2 | 1 | 1 | 1 |
| Found | 1.91 | 1.84 | 1.00$^a$ | 0.76 | 0.58 |

$^a$Reference amino acid

The pherogram at pH 1.9 1 h 1000V shows a broad band at the start and about 2 cm from the starting line on the anode side, and both of them give a ninhydrin positive reaction.

(d)2 Condensation of the fragment to an insulin A-chain in solution

Ddz-Gly-Ile-Val-Glu(OBu$^t$)-Glu(OBzl-Cys(SBu$^t$)-Cys-(Acm)-Ala-Ser(Bu$^t$)-Val-Cys(SBu$^t$)-Ser(Bu$^t$)-Leu-Tyr(Bu$^t$)-Gln-Leu-Glu(OBu$^t$)-Asn-Tyr(Bu$^t$)-Cys(MBzl)-AsnOBu$^t$. [10]

1.1 g (0.5 mMOl) of the insulin A 1-14 [2] described in Section (c)3 is dissolved in 20 ml of absolute dimethyl formamide. The reaction solution is cooled down to $-10°$ C., and treated with 1 equivalent (103 mg) of dicyclohexyl carbodiimide. The mixture is agitated for 10 minutes at $-10°$ C. Then 2 equivalents of 1-hydroxybenzotriazole (135 mg) and 2 equivalents of N-methyl morpholine (0.11 ml) are added, and the temperature is allowed to rise to 0° C. (about 10 minutes). At 0° C., 2 equivalents (1.16 g) of the amine component [9] and 2 equivalents of N-methyl morpholine (0.11 ml) are added, the mixture is heated to room temperature and agitated for 4 days.

Then the reaction solution is concentrated in a vacuum, and separated by means of gel chromatography with methanol, using LH-20, and with a chloroform/methanol gradient, using silica gel K-60 (ready-made column).

The yield amounts to 1.3 g of fully protected A-chain, which corresponds to a conversion of 78%, referred to Fragment III (1-14).

Thin-layer chromatogram (n-butanol/glacial acetic acid/water; 4/1/1): Rf=0.2.

The amino acid analysis (6n HCl, 64 hours, 110° C.) produced the following results:

| | Cys CysSO$_3$H | Asp | Ser | Glu | Gly | Ala | Val | Ile | Leu | Tyr |
|---|---|---|---|---|---|---|---|---|---|---|
| Calc. | 4 | 2 | 2 | 4 | 1 | 1 | 2 | 1 | 2 | 2 |
| Found | 4.12 | 2.21 | 1.86 | 3.94 | 1.01 | 1.02 | 1.00$^a$ | 0.96 | 2.24 | 1.86 |

$^a$Reference amino acid

O.R.D. value: $[\ ]_D^{25}=37.3$ (C=0.05) MeOH.

(d)3 Conversion of Glu(OBzl) into Gln in Position 5

Ddz-Gly-Ile-Val-Glu(OBu$^t$) Gln-Cys(Sbu$^t$)-Cys(Acm)-Ala-Ser(Bu$^t$)-Val-Cys(SBu$^t$)-Ser(Bu$^t$)-Leu-Tyr(Bu$^t$)-Gln-Leu-Glu(OBu$^t$)-Asn-Tyr(Bu$^t$)-Cys(MBzl)-AsnOBu$^t$. [11]

The peptide is dissolved in methanol, and placed in a steel cylinder. The steel cylinder is cooled, and with the exclusion of humidity, liquid ammonia is added. The cylinder is agitated for 4 days at room temperature. In this way, the γ-benzyl ester is split off, with the simultaneous formation of amide. The cleavage solution is concentrated by evaporation in a vacuum at 40° C., and is dissolved in methanol. An insoluble portion remains as a residue.

Crude yield is about 1.1 g.

The insoluble residue is about 0.2 g.

The soluble portion and the solid residue was used together and for further reaction.

(d)4 Formation of the intrachenaric disulfide bridge A$^6$-A$^{11}$

[12]

Ddz—Gly—Ile—Val—Glu(OBu$^t$)—Gln—Cys—Cys(Acm)—Ala—Ser(Bu$^t$)—Val—Cys—

—Ser(Bu$^t$)—leu—Tyr(Bu$^t$)—Gln—Leu—Glu(OBu$^t$)—Asn—Tyr(Bu$^t$)—Cys(MBzl)—AsnOBu The reduction of the disulfide bonds is carried out with tributyl phosphane; the closing of the disulfide bond takes place by air oxidation.

1.3 g of the insulin A-chain [11] is dissolved in 20 ml of propanol/H$_2$O (1.2 1), and N$_2$ is made to flow through the solution. Then 155.6 μl of tributyl phosphane is added. The solution is allowed to react under nitrogen for 48 hours at room temperature. After that the whole reaction solution is poured into 6 l of H$_2$O, which has been adjusted to pH 8 with NH$_3$. Air is passed through the solution for 48 hours. Then concentration is carried out in a vacuum, and LH-20 is separated by gel chromatography.

1.09 g of the material [12] is obtained, which corresponds to a yield of 84%.

Amino acid analysis (110° C. 6 n HCl, 24 hours).

| | Cys CysSO$_3$H | Asp | Ser | Glu | Gly | Ala | Val | Ile | Leu | Tyr |
|---|---|---|---|---|---|---|---|---|---|---|
| Calc. | 4 | 2 | 2 | 4 | 1 | 1 | 2 | 1 | 2 | 2 |
| Found | 3.22 | 1.91 | 2.02 | 3.93 | 1.05 | 1.00$^a$ | 1.58 | 0.67 | 2.11 | 2.21 |

$^a$Reference amino acid

O.R.D. value: $[\beta]_D^{25}=-42.0$ (C=0.1) methanol.

(d)5 Splitting off the protective groups of the combined insulin A-chain

[13]

Gly—Ile—Val—Glu—Gln—Cys—Cys(Acm)—Ala—Ser—Val—Cys—Ser—Leu—Tyr—

Gln—Leu—Glu—Asn—Tyr—Cys(MBzl)—Asn

[MG = 2519,90]

The fully protected insulin A-chains [8] and [12] are combined. In order to split off the protective groups, concentrated trifluoroacetic acid is added to the peptide, and the mixture is allowed to stand for an hour at room temperature. Then the reaction solution is concentrated in a vacuum. The deblocked insulin A-chain is purified again by gel chromatography with Sephadex LH-20/methanol. Finally, the insulin A-chain is freeze-dried, and by so doing 750 mg of pure insulin A-chain is obtained.

Previous oxidation: Performic acid[106], 0° C., 12 hours.

Amino acid analysis: 6 n hydrochloric acid, 110° C., 42 hours.

|  | $CysSO_3H$ | Asp | Ser | Glu | Gly | Ala | Val | Ile | Leu | Tyr |
|---|---|---|---|---|---|---|---|---|---|---|
| Calc. | 4 | 2 | 2 | 4 | 1 | 1 | 2 | 1 | 2 | 2 |
| Found | 3.95 | 1.89 | 1.70 | 3.91 | 1.00[a] | 1.08 | 1.96 | 0.69 | 2.10 | 1.67 |

[a]Reference amino acid

O.R.D. value: $[\alpha]_{25}^D = -76.2$ C=0.5 methanol.

At pH 1.9 1 h 1000 V, the pherogram shows a broad band on the anode side about 3.5 cm from the start line, which reacts $Cl_{I/II}$-positively.

(e) The combination of purified synthetic bovine insulin A-chain with natural bovine insulin B-chain (e)1 The splitting off of the MBzl-protective group with HF/pyridine 40.8 mg of the synthetic bovine insulin A-chain, formed in the above manner, is dissolved in 2 ml of HF/pyridine. The cleavage reagent serves, at the same time, as a solvent. 0.25 ml of anisol is added as a cation trap. After 60 minutes of reaction time at room temperature, the peptide, which has been reduced to Cys 20, is precipitated with ether. A sticky white precipitate is formed, which is thoroughly washed with ether several times.

The deblocked A-chain is then immediately dissolved in 3 ml of 30 percent acetic acid.

53.4 mg of reduced B-chain has already been dissolved previously in 2 ml of 30 percent acetic acid.

The prepared solution is then added to the reaction solvent and titrated with 0.1 n iodine solution until the color of the iodine remains constant after about 4 minutes. The excess iodine is back titrated with ascorbic acid until the reaction solution is colorless.

(e)2 Purification of semisynthetic bovine insulin

The reaction solution is immediately fractionated with the use of Sephadex G-50 in acetic acid (column 1.50×60 cm). Fractions 3, 4, 5, and 6 are individually freeze-dried, and compared by electrophoresis with authentic bovine insulin. Fractions 3, 4, and 5 contain bovine insulin which has been identified by electrophoresis and thin layer chromatography. The crude yield amounts to 24.2 mg (25%). Biological tests are carried out with the crude product.

The various fractions are again individually passed through, in 1 percent acetic acid, a biogel-P-6-column (column 2 m×0.8 cm). The fractions that contain insulin after this second separation are combined, and again passed through the same column. The main fraction now contains 18.2 mg of insulin (yield 20%).

With this, a biological test was carried out again. Previous oxidation: performic acid [106], 0° C., 12 hours Amino acid analysis: 6 n HCl, 110° C., 42 hours

|  | $CysSO_3H$ | Asp | Thr | Ser | Glu | Pro | Gly | Ala |
|---|---|---|---|---|---|---|---|---|
| Calc. | 6 |  | 3 | 1 | 3 | 7 | 1 | 4 | 3 |
| Found | 5.91 |  | 3.70 | 0.86 | 2.71 | 6.75 | 0.91 | 4.03 | 3.23 |

|  | Val | Ile | Leu | Tyr | Phe | His | Lys | Arg |
|---|---|---|---|---|---|---|---|---|
| Calc. | 5 | 1 | 6 | 4 | 3 | 2 | 1 | 1 |
| Found | 5.12 | 0.86 | 6.00[a] | 3.73 | 3.38 | 1.89 | 1.11 | 1.06 |

[a]Reference amino acid

FIG. 5 represents a photomicrograph of the zinc complex of the fully active bovine insulin obtained.

With the aid of the process according to the present invention, insulin and insulin analogs can be produced with precision, which have the intrachenaric and/or the interchenaric disulfide rings in natural or unnatural arrangement, and which are of great importance for therapeutic purposes. Thus, the antiparallel variants of insulin, especially, with a natural or unnatural arrangement of the intrachenaric small disulfide ring, represents interesting storage forms of insulin, since under physiological conditions, they are very slowly converted into active insulin. The insulin that is built up on and bound to the polymeric carrier, with a natural or unnatural arrangement of the intrachenaric and/or interchenaric disulfide rings, also represents such an especially long-lived, unphysiological insulin storage form.

The object of the present invention, therefore, is also drugs which contain the insulin products obtained with the aid of process according to the present invention, in accordance with claims 2 to 18, with a natural or unnatural arrangement of the intra- and/or interchenaric disulfide bridges, if necessary in combination with the usual, pharmaceutically acceptable binders, carriers, and/or adjuvants.

It will be understood that the specification and examples are illustrative but not limitative of the present invention and that other embodiments within the spirit and scope of the invention will suggest themselves to those skilled in the art.

What is claimed is:

1. Process for the selective formation of at least two disulfide bridges in a polypeptide which process comprises treating a polypeptide starting material carrying at least four SH-groups to mask at least one of two of said SH-groups, intended to form a first disulfide bridge, with a p-methoxybenzyl protective group and to mask at least one SH-group of each further pair of SH-groups intended to form one or more further disulfide bridges, with an acetamido methyl protective group, then splitting off said p-methoxybenzyl protective group with pyridine-polyhydrogen fluoride in the presence of anisol to produce that first disulfide bridge, and then treating the polypeptide with iodine in an acid solution to produce said disulfide bridge-containing polypeptide by forming said one or more further disulfide bridges.

2. Process as claimed in claim 1 wherein the formation of two or more disulfide bridges is conducted in the presence of already existing disulfide bridges.

3. Process as claimed in claim 1 wherein said polypeptide is a synthetic polypeptide.

4. Process as claimed in claim 1 wherein said polypeptide is a natural polypeptide.

5. Process as claimed in claim 2, wherein an already existing disulfide bridge is formed by reductive splitting-off of two tertiary butyl mercapto protective groups, protecting two further SH-groups carried by said polypeptide starting material, with tributyl phosphane under inert gas and selective oxidation with oxygen prior to forming the said first and further disulfide bridges.

6. Process for the selective formation of at least three disulfide bridges in a polypeptide which process comprises treating a polypeptide starting material, carrying at least 6 SH-groups, to mask two of said SH-groups intended to form a first disulfide bridge with tertiary butyl mercapto protective groups, to mask at least one of two further of said SH-groups, intended to form a second disulfide bridge, with an acetamido methyl protective group, and to mask at least one SH-group of each further pair of SH-groups, intended to form one or more further disulfide bridges, with an acetamido methyl protective group, then splitting off said two tertiary butyl mercapto protective groups with tributyl phosphane under innert gas and selective oxidation with oxygen, thereby forming that first disulfide bridge, then splitting-off said p-methoxybenzyl protective group with pyridine-polyhydrogen fluoride in the presence of anisol to produce that second disulfide bridge, and then treating the polypeptide with iodine in an acid solution to produce said disulfide bridge-containing polypeptide by forming said one or more further disulfide bridges.

7. Process as claimed in claim 1 wherein active human insulin is prepared by reacting a synthetic insulin A-chain having an acetamido methyl protective group in the $A^7$-position and a p-methoxybenzyl protective group in the $A^{20}$-position and with an equimolar quantity of synthetic or natural reduced insulin B-chain.

8. Process as claimed in claim 7 wherein an insulin B-chain is used having an acetamido methyl protective group in the $B^7$-position and a p-methoxybenzyl protective group in the $B^{19}$-position.

9. Process as claimed in claim 7 wherein a synthetic insulin A-chain is used in which the small interachenaric disulfide ring has been formed by reductive splitting-off of the tertiary butyl mercapto protective groups in the $A^6$- and $A^{11}$-positions with tributyl phosphane under nitrogen and selective oxidation with air.

10. Process as claimed in claim 7 wherein the B-chain of bovine insulin is used as the natural insulin, modified at the C-terminus.

11. Process as claimed in claim 7 wherein $A^6$-$A^7$, $A^{11}$-$B^7$-cystine insulin is prepared from synthetic $A^6$-$A^7$ insulin A-chain having an acetamido methyl protective group in the $A^{20}$-position and a p-methoxybenzyl protective group in the $A^{11}$-position.

12. Process as claimed in claim 1 wherein $A^6$-$A^7$, $A^{11}$-$B^7$-cystine insulin is prepared from synthetic $A^6$-$A^7$ insulin A-chain having an acetamido methyl protective group in the $A^{11}$-position and a p-methoxybenzyl protective group in the $A^{20}$-position.

13. Process as claimed in claim 1 wherein the disulfide bridge formation is effected by oxidation with iodine in 30% acetic acid.

14. Process as claimed in claim 1 wherein the splitting off the p-methoxybenzyl protective group is carried out in pyridine polyhydrogen fluoride (HF/pyridine) as solvent and reagent.

15. Process as claimed in claim 1 wherein antiparallel $A^6$-$A^{11}$, $A^7$-$B^{19}$, $A^{20}$-$B^7$-cystine insulin is produced by reacting a natural or synthetic $A^6$-$A^{11}$ insulin A-chain having an acetamido methyl protective group in the $A^7$-position and a p-methoxybenzyl protective group in the $A^{20}$-position, with a natural or synthetic insulin B-chain in reduced form or having an acetamido methyl protective group in the $B^{19}$-position and a p-methoxybenzyl protective group in the $B^7$-position.

16. Process as claimed in claim 1 wherein antiparallel $A^6$-$A^{11}$, $A^7$-$B^{19}$, $A^{20}$-$B^7$-cystine insulin is produced by reacting a natural or synthetic $A^6$-$A^{11}$ insulin A-chain having an acetamido methyl protective group in the $A^{20}$-position and a p-methoxybenzyl protective group in the $A^7$-position, with a natural or synthetic insulin B-chain in reduced form having an acetamido methyl protective group in the $B^7$-position and a p-methoxybenzyl protective group in the $B^{19}$-position.

17. Process as claimed in claim 1 wherein antiparallel $A^6$-$A^{11}$, $A^7$-$B^{19}$, $A^{20}$-$B^7$ cystine insulin is produced by reacting a synthetic $A^7$-$A^{11}$ insulin A-chain having an acetamido methyl protective group in the $A^6$-position and a p-methoxybenzyl protective group in the $A^{20}$-position with a natural or synthetic insulin B-chain in reduced form having an acetamido methyl protective group in the $B^{19}$-position and a methoxybenzyl protective group in the $B^7$-position.

18. Process as claimed in claim 1 wherein antiparallel $A^6$-$A^{11}$, $A^7$-$B^{19}$, $A^{20}$-$B^7$-cystine insulin is produced by reacting a synthetic $A^6$-$A^{11}$ insulin A-chain having an acetamido methyl protective group in the $A^{20}$-position and a p-methoxybenzyl protective group in the $A^7$-position with a natural or synthetic insulin B-chain in reduced form or having an acetamido methyl protective group in the $B^7$-position and a p-methoxybenzyl protective group in the $B^{19}$-position.

19. Process as claimed in claim 1 wherein antiparallel $A^6$-$A^{11}$, $A^7$-$B^{19}$, $A^{20}$-$B^7$-cystine insulin is produced by reacting a synthetic $A^6$-$A^{11}$ insulin A-chain having an acetamido methyl protective group in the $A^7$-position and a p-methoxybenzyl protective group in the $A^{20}$-position with a natural or synthetic insulin B-chain in reduced form having an acetamido methyl protective group in the $B^{19}$-position and a p-methoxybenzyl protective group in the $B^7$-position.

20. Process as claimed in claim 1 wherein antiparallel $A^6$-$A^7$, $A^{11}$-$B^{19}$, $A^{20}$-$B^7$-cystine insulin is produced by reacting a synthetic $A^6$-$A^7$ insulin A-chain having an acetamido methyl protective group in the $A^{20}$-position and a p-methoxybenzyl protective group in the $A^{11}$-position with a natural or synthetic insulin B-chain in reduced form or having an acetamido methyl protective group in the $B^7$-position and a p-methoxybenzyl protective group in the $B^{19}$-position.

21. Process as claimed in claim 1 wherein antiparallel $A^6$-$A^{11}$, $A^7$-$B^{19}$, $A^{20}$-$B^7$-cystine insulin is produced by reacting a natural or synthetic insulin A-chain, with the intrachenaric disulfide ring in the $A^6$-$A^{11}$-position, the $A^7$-$A^{11}$-position or in the $A^6$-$A^7$-position in a parallel or antiparallel manner with a natural or synthetic insulin B-chain in reduced form or having acetamido methyl protective groups and a p-methoxybenzyl protective groups, where the specified A-chain by a reactive anchor bond is linked to a polymeric carrier.

22. Process as claimed in claim 21 wherein polystyrene cross-linked with divinylbenzene is used as the polymeric carrier.

23. Process as claimed in claim 22 wherein a polystyrene gel is used, which is cross-linked with 0.1% to 0.8% divinylbenzene.

24. Process as claimed in claim 23 wherein 0.5 divinylbenzene is used.